United States Patent [19]
Jacobson et al.

[11] Patent Number: 6,062,261
[45] Date of Patent: May 16, 2000

[54] MICROFLUIDIC CIRCUIT DESIGNS FOR PERFORMING ELECTROKINETIC MANIPULATIONS THAT REDUCE THE NUMBER OF VOLTAGE SOURCES AND FLUID RESERVOIRS

[75] Inventors: Stephen C. Jacobson; J. Michael Ramsey, both of Knoxville, Tenn.

[73] Assignee: Lockheed Martin Energy Research Corporation, Oak Ridge, Tenn.

[21] Appl. No.: 09/212,217

[22] Filed: Dec. 16, 1998

[51] Int. Cl.[7] .................................................. G01N 27/26
[52] U.S. Cl. .......................... 137/827; 137/806; 204/601; 204/607
[58] Field of Search ................................... 137/826, 827, 137/806, 88; 204/451, 600, 601, 604

[56] References Cited

U.S. PATENT DOCUMENTS

| | | |
|---|---|---|
| 4,908,112 | 3/1990 | Pace . |
| 5,073,239 | 12/1991 | Hjerten . |
| 5,092,973 | 3/1992 | Zare et al. . |
| 5,110,431 | 5/1992 | Moring . |
| 5,116,471 | 5/1992 | Chien et al. ............................. 204/604 |
| 5,126,022 | 6/1992 | Soane et al. . |
| 5,132,012 | 7/1992 | Miura et al. . |
| 5,141,621 | 8/1992 | Zare et al. . |
| 5,180,480 | 1/1993 | Manz . |
| 5,250,263 | 10/1993 | Manz . |
| 5,296,114 | 3/1994 | Manz . |
| 5,328,578 | 7/1994 | Gordon .................................... 204/604 |
| 5,376,252 | 12/1994 | Ekström et al. . |
| 5,603,351 | 2/1997 | Cherukuri et al. ....................... 204/601 |
| 5,750,015 | 5/1998 | Soane et al. . |
| 5,785,831 | 7/1998 | Bek .......................................... 204/601 |
| 5,858,187 | 1/1999 | Ramsey et al. .......................... 204/601 |

FOREIGN PATENT DOCUMENTS

| | | |
|---|---|---|
| 0356160 | 2/1990 | European Pat. Off. . |
| 0620432 | 10/1994 | European Pat. Off. . |
| 2191110 | 12/1987 | United Kingdom . |

OTHER PUBLICATIONS

S.C. Jacobson, "Effects of column geometry on the performance of u–chip electrophoresis devices", Anal. Chem. Div. and Health and Safety Res. Div., Oak Ridge Natl. Lab., Oak Ridge TN, Aug. 25, 1993.

T. L. Hoopman, "Microchanneled Structures", Microstructures, Sensors, and Actuators, The American Soc. of Mechanical Engineers, DSC–vol. 19, ®1990.

S. C. Jacobson, "High speed separations on a u–chip", Anal. Chem. Div., Oak Ridge Natl. Lab., Oak Ridge TN, Aug. 25, 1993.

D. J. Harrison et al., "Micromachining a Miniaturized Capillary Electrophoresis–Based Chemical Analysis System on a Chip", Science, vol. 261, Aug. 13, 1993.

(List continued on next page.)

*Primary Examiner*—A. Michael Chambers
*Attorney, Agent, or Firm*—Dann, Dorfman, Herrell and Skillman, P.C.

[57] ABSTRACT

A microfabricated device and method for proportioning and mixing electrokinetically manipulated biological or chemical materials is disclosed. The microfabricated device mixes a plurality of materials in volumetric proportions controlled by the electrical resistances of tributary reagent channels through which the materials are transported. The microchip includes two or more tributary reagent channels combining at one or more junctions to form one or more mixing channels. By varying the geometries of the channels (length, cross section, etc.), a plurality of reagent materials can be mixed at a junction such that the proportions of the reagent materials in the mixing channel depend on a ratio of the channel geometries and material properties. Such an approach facilitates voltage division on the microchip without relying on external wiring schemes and voltage division techniques external to the microchip. Microchannel designs that provide the necessary voltage division to accomplish electrokinetic valving operations using a single voltage source and a switch are also described. In addition, microchannel designs that accomplish fluidic operation utilizing a minimal number of fluidic reservoirs are disclosed.

22 Claims, 13 Drawing Sheets

OTHER PUBLICATIONS

M. Foret et al., "Electric Sample Splitter for Capillary Zone Electrophoresis", Journ. of Chromatography, Elsevier Science Pub., The Netherlands, 1985.

C. S. Effenhauser, Glass Chips for High–Speed Capillary Electrophoresis Separations with Submicrometer Plate Heights, Anal. Chem., vol. 65, No. 19, Oct. 1, 1993.

D. J. Harrison et al., "Capillary Electrophoresis and Sample Injection Systems Integrated on a Planar Glass Chip", Anal. Chem., vol. 64, No. 17, Sep. 1, 1992.

S. C. Jacobson et al., "Effects of Injection Schemes and Column Geometry on the Performance of Microchip Electrophoresis Devices", Anal. Chem., vol. 66, 1994.

6,062,261

MICROFLUIDIC CIRCUIT DESIGNS FOR PERFORMING ELECTROKINETIC MANIPULATIONS THAT REDUCE THE NUMBER OF VOLTAGE SOURCES AND FLUID RESERVOIRS

This invention was made with government support under contract DE-AC05-96OR22464 awarded by the U.S. Department of Energy to Lockheed Martin Energy Research Corporation and the government has certain rights in this invention.

FIELD OF THE INVENTION

The invention relates to a microchip design for the electrokinetic manipulation of chemical and biological materials. More specifically, this invention relates to a microchip device in which the reagent and mixing channels are dimensioned to proportion the electrokinetic driving forces without the need for external voltage division schemes or multiple independent power supplies, and to reduce the number of fluidic reservoirs needed for operability, relative to known microchip devices. Similar advantages are provided by embodiments for performing dispensing operations.

BACKGROUND OF THE INVENTION

The mixing of two or more liquid-phase materials or the dispensing of a reagent material on a microchip is accomplished by controlling the electric potentials applied to the various reservoirs to electrokinetically drive the materials housed therein through the channels of the microchip. Heretofore, this process has required external voltage control means such as a power supply employing a voltage divider network, or programmable power supplies. Such external voltage sources are utilized to effect valving and mixing phenomena in the channel manifold of a microfabricated device.

Because of the configurations of the known voltage sources it has been necessary to use a plurality of voltage source leads and corresponding microchip contact points in order to apply the multiple electric potentials. The number of such sources and accompanying hardware to effect electrokinetic phenomena can be quite bulky and require complex architectures to control. This is most evident in highly parallel architectures, especially if each node requires a different applied potential from an external source.

Therefore, a need has arisen for a microchip that is capable of mixing sample material in various proportions and dispensing variable volumes of a sample material in which the fluid material is driven electrokinetically by a single high voltage supply. In this way, excess wires and circuitry needed for a voltage division scheme or the complexity of multiple programmable power supplies can be eliminated and the microchip can be implemented with fewer fluidic reservoirs compared to the known designs.

SUMMARY OF THE INVENTION

The present invention provides a microfabricated device for liquid phase chemical and biological analysis. A device in accordance with the invention includes a substrate on which a series of microchannels are formed. A cover plate is bonded to the substrate to close the open side of the microchannels. Reservoirs are in fluidic communication with the end of the microchannels. The reservoirs are in electrical contact with a high voltage power source providing electrical potential for electrokinetically mixing and/or dispensing fluidic materials contained therein.

The microchip includes a series of tributary channel junctions ("tees" and/or four-way intersections) wherein at least two tributary reagent microchannels communicate with a common mixing microchannel. The tributary reagent channels have either different cross sectional areas, different lengths, or both and, therefore different electrical resistances. The material in the tributary reagent channels is mixed at a channel junction depending on the ratio of the channel electrical resistances. Such an approach can handle all or a portion of the voltage division on the microchip without using techniques external to the microchip. The mixing of two or more materials is achieved using electrophoretic and/or electroosmotic transport. In accordance with another aspect of the present invention, there is provided a microfabricated device that is capable of dispensing variable volumes of a sample material. In accordance with a further aspect of this invention, the tributary channels are formed so that a reduced number of material reservoirs can be utilized when performing multiple ratio assays or reactions.

A first category of microfabricated devices in accordance with the present invention provides a voltage division technique that utilizes a reduced number of different external voltage sources to effect microfluidic reagent mixing relative to previous devices. A second category of microfabricated devices in accordance with this invention allows dispensing of samples on a multi-port device with a single external high voltage supply and switch.

BRIEF DESCRIPTION OF THE DRAWINGS

The foregoing summary, and the following detailed description, will be best understood when read in conjunction with the attached drawings, in which.

DETAILED DESCRIPTION

Figure 1:
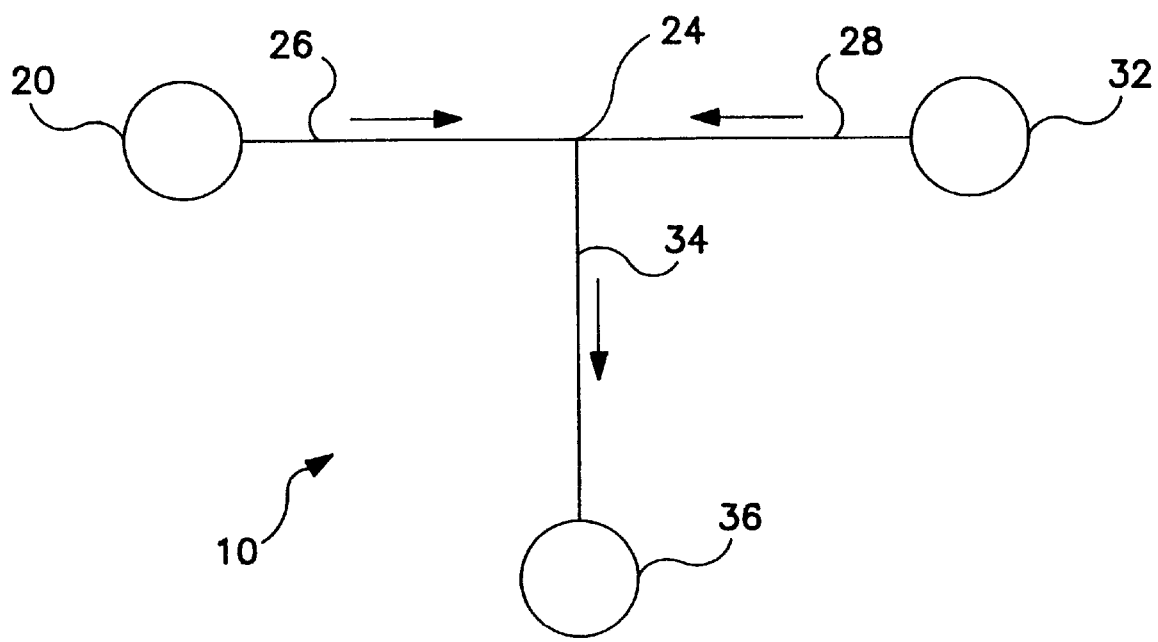
FIG. 1 is a schematic diagram showing a mixing junction in accordance with this invention.

A microfabricated device in accordance with the present invention is described in connection with four embodiments. The embodiments demonstrate the mixing of two or more reagent materials by way of a series of tributary channel junctions wherein at least two tributary reagent microchannels communicate with a common mixing microchannel. The tributary reagent channels have the same cross sectional area but different lengths and, therefore different electrical resistances. A comparable device could be fabricated using similar channel length but different cross-sectional areas or a combination of the two strategies. The amount of reagent supplied by each tributary channel is dependent upon the ratio of the channel lengths and the electrokinetic transport properties of the materials within the channels. Electrokinetic transport properties depend on a number of parameters that can be reagent specific such as ionic strength, conductivity, dielectric constant, and zeta potential. Variations in such parameters can be taken into account in designing structures such as described in this application, provided that the parameters are known to the designer. If parameters for some materials are not known, than a device can be designed to minimize the influence of such material on the functioning of the device. For the embodiments described hereinbelow, it is assumed that the electrokinetic transport properties are uniform throughout the structure, although it is recognized that such is not a necessary assumption in order to make an actual device.

In the first embodiment, material in the tributary reagent channels is mixed at a common junction. The amount of reagent supplied by each tributary channel is dependent upon the ratio of the channel lengths. The design approach for this embodiment can handle all the voltage division on the microchip without using techniques external to the microchip. The mixing of two or more materials is achieved using electrophoretic and/or electroosmotic transport.

In accordance with a second embodiment of this invention, the tributary channel length is varied by use of a plurality of mixing channels and a high voltage switch operably connected thereto. The switch has a plurality of contact positions each of which is associated with a combination of a mixing channel and tributary channels. A desired configuration for the tributary channels and mixing channel is selected by placing the switch in the corresponding switch position. In this way, a change in the switch position effects a change in the proportion of reagent materials dispensed through the tributary channels.

In a third embodiment of this invention, there is provided a microfabricated device employing a valve that is capable of dispensing variable quantities of a sample material. In accordance with a fourth embodiment of this invention, a microfabricated device is provided for performing a plurality of dilution experiments with a minimized number of reagent and diluent material reservoirs and a reduced number of voltage sources.

Volumetric Proportioning

Referring now to FIG. 1, a mixing junction or "tee" 10 includes a sample reservoir 20, buffer reservoir 32, sample channel 26, buffer channel 28, a mixing channel 34, and waste reservoir 36. When a single electrical potential is applied to the sample reservoir 20 and buffer reservoir 32 relative to waste reservoir 36, the fluidic materials from the sample reservoir and the buffer are mixed in the tee junction 24 in a ratio that is inversely proportional to the resistances of the sample channel 26 and buffer channel 28. When the sample channel 26 and buffer channel 28 have the same cross-sectional area, the electrical resistance is directly proportional to the channel lengths. Thus, when the sample and buffer channels have the same lengths and the same cross-sectional areas, the sample and buffer materials are transported to and mixed in equal proportions at junction 24 under the assumption of homogeneous conductivities. When the sample and buffer channels have different lengths, the sample and buffer materials are transported and mixed in a ratio that is proportional to the length of the buffer channel relative to the combined lengths of the sample and buffer channels. Alternatively, the cross-sectional areas of the sample and buffer channels can be dimensioned to provide the desired mixing proportions because the resistance of the respective channel is inversely proportional to the cross-sectional area of the channel. Of course, it is also contemplated that the channel resistance can be selected by adjusting both the channel lengths and the channel cross-sectional areas to provide the desired electric fields for transporting and mixing the sample and buffer materials.

Figure 2:
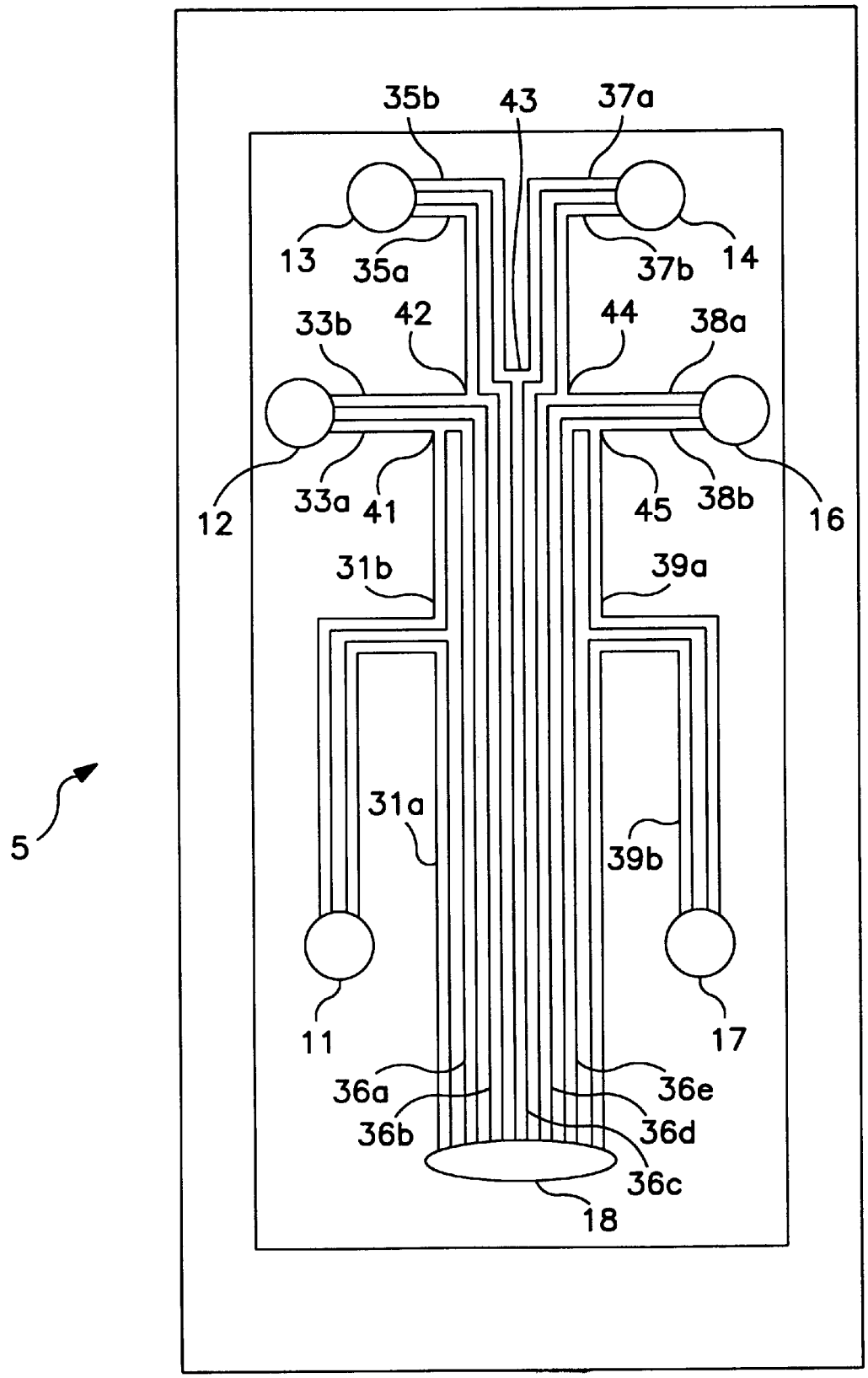
FIG. 2 is a schematic diagram of a fluidic microchip for mixing reagents in accordance with the present invention.

Referring now to FIG. 2, there is shown a working example of a fluidic microchip in accordance with this invention. The microfabricated device 5 includes a first buffer reservoir 11, a first sample reservoir 12, a second buffer reservoir 13, a second sample reservoir 14, a third buffer reservoir 16, a third sample reservoir 17, and a waste reservoir 18. A first buffer channel 31a connects the first buffer reservoir 11 with the waste reservoir 18. A second buffer channel 31b connects the first buffer reservoir 11 with a first sample channel 33a that is in fluid communication with the first sample reservoir 12. The intersection of the second buffer channel 31b and first sample channel 33a forms a "tee" junction 41 with a first waste channel 36a that is in fluid communication with the waste reservoir 18. In like manner the second buffer reservoir 13 is connected to the first and second sample reservoirs 12 and 14 and to the waste reservoir 18 through channels 33b, 35a, 35b, 36b, 36c, and 37a. Further, the third buffer reservoir 16 is connected to the second and third sample reservoirs 14 and 17 and to the waste reservoir 18 through channels 37b, 38a, 38b, 39a, 36d, and 36e. The dimensions of the channels 31b, 33a, 33b, 35a, 35b, 37a, 37b, 38a, 38b, and 39a are selected to provide respective electrical resistances that result in desired mixing ratios of the various sample and buffer materials at the corresponding junctions 41, 42, 43, 44, and 45, for transport to the waste reservoir 18 along the waste channels 36a, 36b, 36c, 36d, and 36e, respectively.

Microchip 5 is designed and fabricated from a solid substrate material, preferably, glass. However, such materials as silicon may also be used because of the well developed technology permitting its precise and efficient fabrication. Although silicon has problems associated with electrical conductivity, such limitations can be offset by employing insulating layers. Other materials such as polymers, quartz, fused silica, sapphire, or plastics are also suitable as substrate materials. The surface of the microfabricated device 5 is covered and sealed by a cover plate. The substrate includes a microfabricated surface containing channels and reservoirs for facilitating the electrokinetic transport of biological and chemical materials from the reservoirs through the channels of the microfabricated device 5.

The microchip device 5 is fabricated using micromachining methods known to those skilled in the art. The micromachining methods available include film deposition processes such as spin coating and chemical vapor deposition, laser fabrication or photolithographic techniques such as visible, ultraviolet (UV), or X-ray processes, or etching methods which may be performed by either wet chemical processes or plasma processes. Preferably, the microchannel configurations of microchip 5 are transferred onto the substrate material using a positive photoresist, photomask, and UV exposure. The channels are etched into the substrate in a dilute, stirred $HF/N_4HF$ bath.

The mixing of two or more materials contained in the microfabricated channels of a microchip device according to this invention is achieved using electrokinetic transport. A microchip device in accordance with this invention having a structure like that shown in FIG. 2 was fabricated as described above. The sample and buffer channels were dimensioned to proportion two streams in five different channels to demonstrate a multiple dilution experiment. Channels 31a and 39b do not have mixing junctions. The sample and buffer channel lengths to each tee junction were selected to provide a dilution ratio (sample/(sample+buffer)) of 0 in Channel 31a, 0.83 in Channel 36a, 0.68 in Channel 36b, 0.52 in Channel 36c, 0.34 in Channel 36d, 0.16 in Channel 36e, and 1 in Channel 39b. An electrical potential is applied to the sample and buffer reservoirs 11–16 relative to the waste reservoir 18 to electrokinetically transport the materials through the microchip channel manifold. The electrical potential was applied through platinum wire electrodes which were connected to a single high voltage source. The required electric field strength to enable electroosmotic flow is often between 100 V/cm and 1000 V/cm.

To demonstrate the proportioned mixing of the pairs of tributary channels on the microchip device 5, a dilution experiment of a sample material in a buffer material was performed. In Table 1, the lengths of the respective sample and buffer channels are listed with the calculated dilution ratio (% Sample Calculated) and the measured dilution ratio (% Sample Measured) for each channel. The experiment was performed by placing the same sample material in reservoirs corresponding to first sample reservoir 12, second sample reservoir 14, and third sample reservoir 17. A diluent was placed in the first buffer reservoir 11, second buffer reservoir 13, and third buffer reservoir 16. A 1 kV potential was applied to the buffer and sample reservoirs and the waste reservoir 18 was maintained at ground potential.

Microchip performance was monitored by laser induced fluorescence (LIF) using a charge coupled device (CCD) for imaging and an argon ion laser beam (514.5 mn, ~100 mW) for excitation. The fluorescence signal was collected using an optical microscope, filtered spectrally (550 nm cut-on), and measured by the CCD. The diluent was 10 mM sodium tetraborate, and the sample solution was rhodamine B (40 $\mu$M) in 10 mM of the buffer solution.

Figure 3:
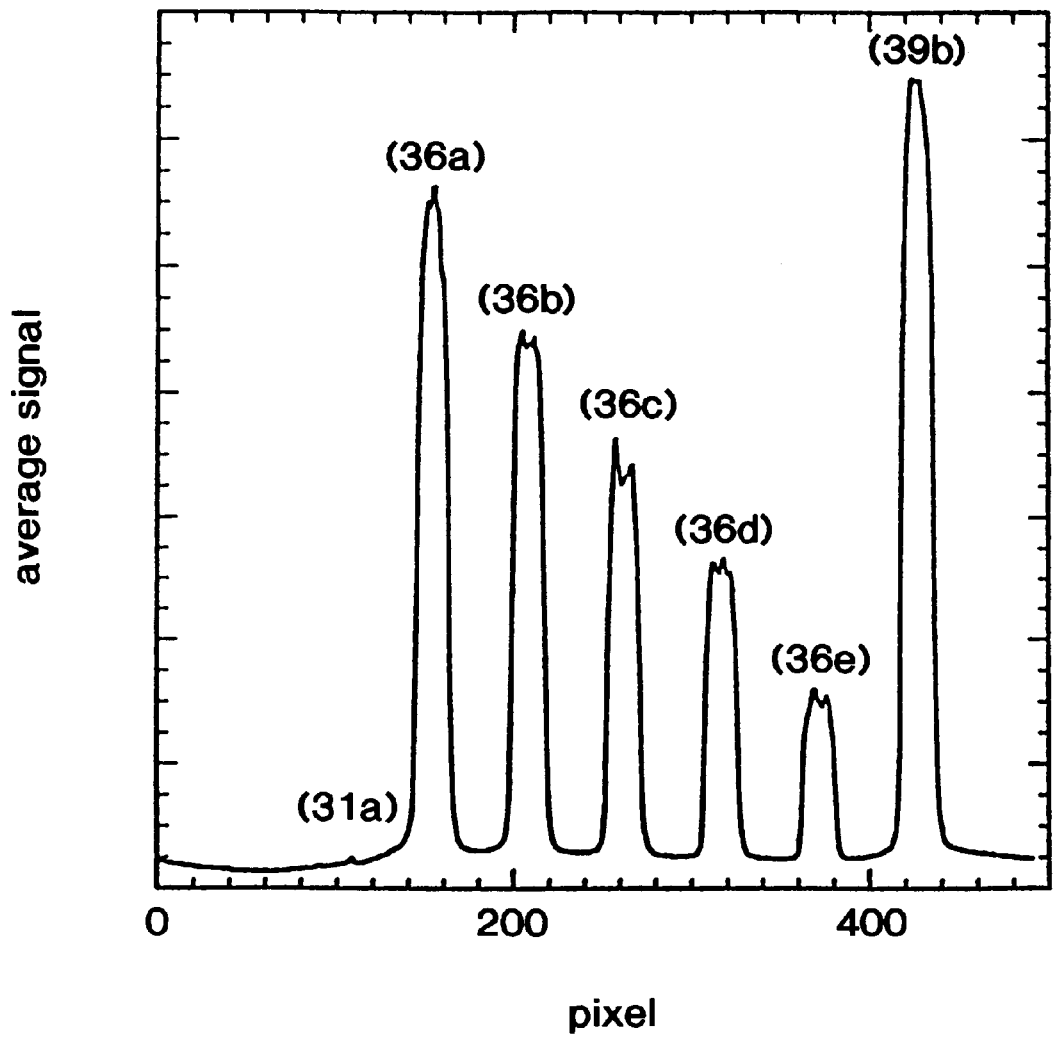
FIG. 3 is a graph of the average fluorescence signals in the waste channels of the fluidic microchip shown in FIG. 2.

Referring now to FIG. 3, the average fluorescence signal is plotted as a function of the lateral position across the waste channels. From this plot, the integrated area allows the determination of the experimental dilution ratios which are shown in Table 1. The data presented in Table 1 show good correlation between the predicted values and the actual values. For channels 36d and 36e, the actual ratios are higher than expected. As the quality of the substrate machining improves, it is expected that the ratios will match more closely. Also, the microchips prepared in accordance with this invention can be calibrated following fabrication to handle small differences in channel dimensions which affect the channel resistance.

TABLE 1

| Channel | Length Sample | Length Buffer | Length Mixing | % Sample, Calculated | % Sample, Measured |
|---------|---------------|---------------|---------------|----------------------|---------------------|
| 31a     | —             | 44.8          | —             | 0                    | 0                   |
| 36a     | 4.9           | 24.5          | 39.7          | 83                   | 84                  |
| 36b     | 5.0           | 10.4          | 39.8          | 68                   | 67                  |
| 36c     | 9.6           | 10.5          | 39.9          | 52                   | 51                  |
| 36d     | 9.5           | 4.8           | 39.8          | 34                   | 36                  |
| 36e     | 24.8          | 4.7           | 39.7          | 16                   | 19                  |
| 39b     | 45.1          | —             | —             | 100                  | 100                 |

*length in mm

Figure 2A:
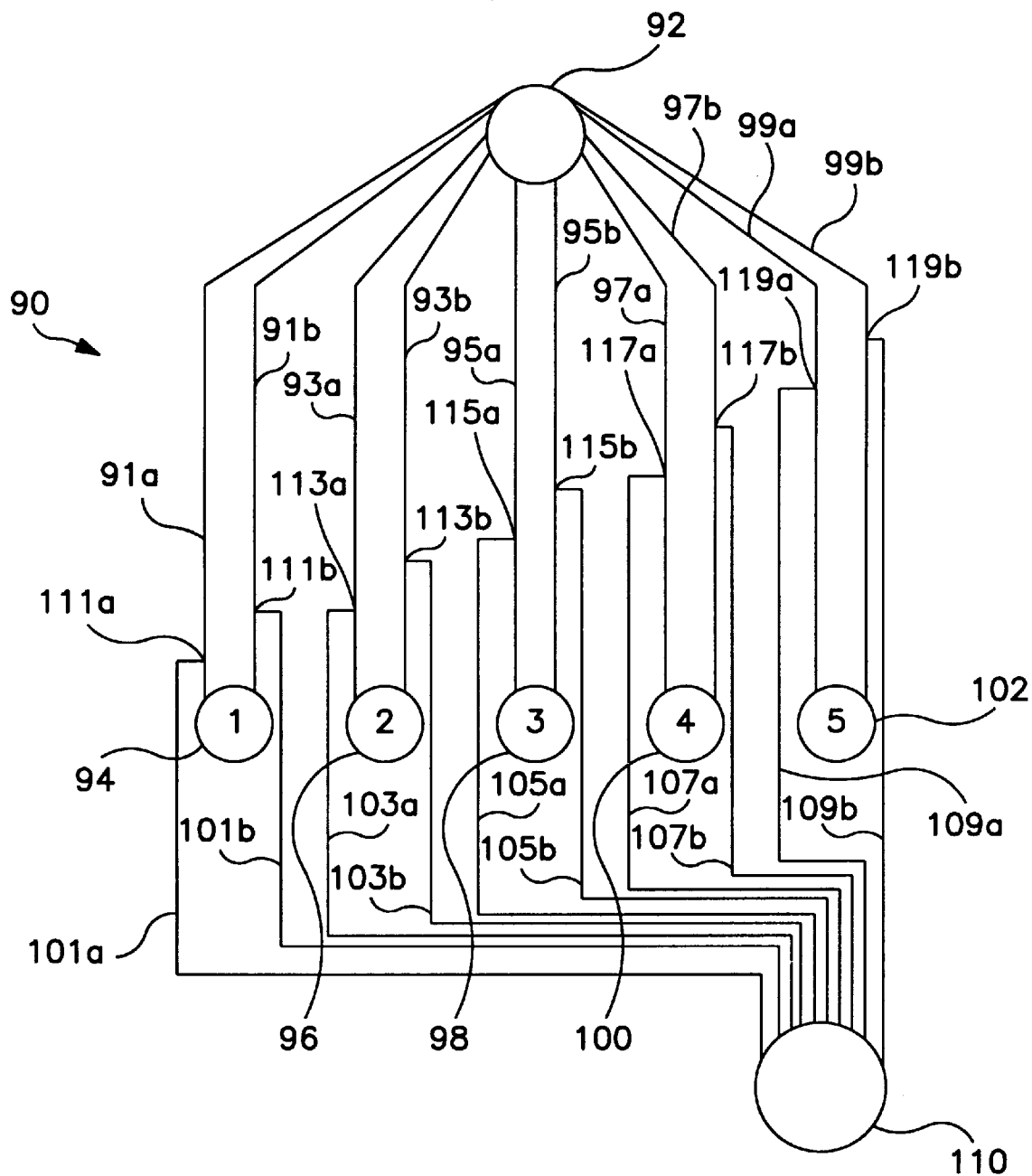
FIG. 2a is a schematic diagram of an alternative embodiment of the fluidic microchip shown in FIG. 2.

Referring now to FIG. 2a, an alternative embodiment of a microchip device in accordance with the present invention is shown having multiple sets of mixing junctions configured for minimizing the number of material reservoirs. The device 90 includes a single sample reservoir 92, a plurality of buffer reservoirs 94, 96, 98, 100, and 102, and a waste reservoir 110. The sample material is loaded into the sample reservoir 92. A common buffer, reagent, or various buffers or reagents are loaded into the buffer reservoirs 94–102. Respective pairs of sample channels 91a, 91b, 93a, 93b, 95a, 95b, 97a, 97b, and 99a, 99b interconnect the sample reservoir 92 to each of the plurality of buffer/reagent reservoirs 94–102. Corresponding pairs of mixing channels 101a, 101b, 103a, 103b, 105a, 105b, 107a, 107b, and 109a, 109b interconnect each sample channel with the waste reservoir 110. The mixing channels intersect the sample channels at mixing junctions 111a, 111b, 113a, 113b, 115a, 115b, 117a, 117b, and 119a, 119b, respectively. This arrangement allows a large number of simultaneous, fixed dilutions of the sample material to be performed with one or more buffer solutions. The cross-sectional areas and lengths of the channel segments forming the mixing junctions are dimensioned to provide mixing of the sample and buffer materials in different, preselected proportions at each of the mixing junctions. In this way, the device 90 minimizes the number of reservoirs required to do the multiple dilutions of a single sample within a two dimensional layout, i.e., without crossing of channels. In general, to perform N dilutions, N/2+2 reservoirs are required. The value is rounded up to the next higher integer if N is an odd number. In a variation of the embodiment shown in FIG. 2a, the plurality of buffer reservoirs are combined into a single reservoir by using sufficiently small vertical access conduits (vias) through the microchannel coverplate and a buffer reservoir having a sufficiently large cross section to access the vias. Alternatively, vias could be used to communicate between multiple layers of microchannels to allow the reduction of the plurality of buffer reservoirs into a single reservoir. The multiple layers of microchannels would allow channels to cross over the tops of each other similar to the constructs used in multilayer printed circuit boards.

Figure 4:
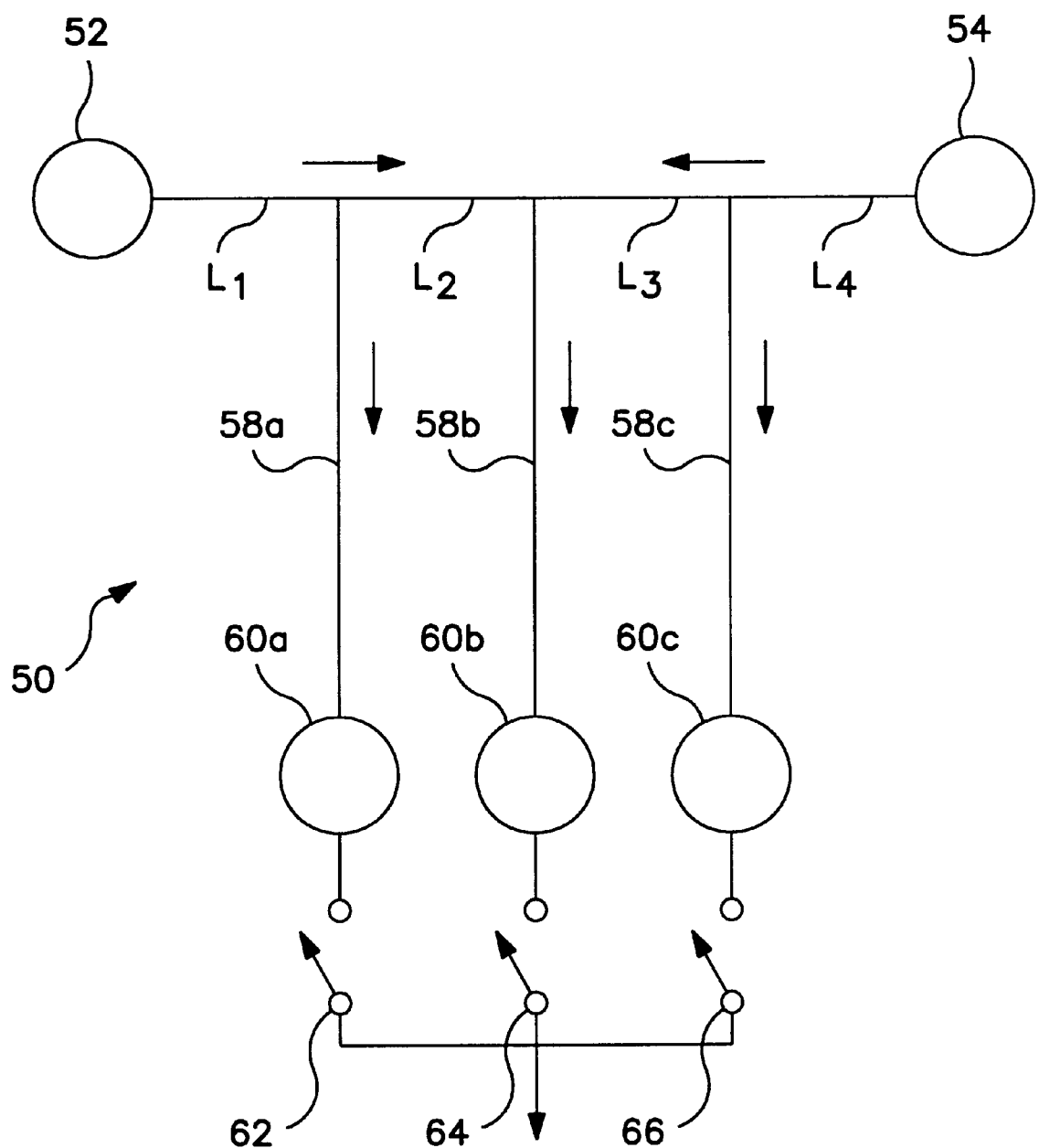
FIG. 4 is a schematic diagram of an alternative embodiment of a fluidic microchip in accordance with the present invention.

Referring now to FIG. 4, there is shown a further embodiment of a microchip device according to this invention. A microchip 50 includes sample reservoir 52, buffer reservoir 54, and waste reservoirs 60A–60C. Sample and buffer reservoirs 52 and 54 supply fluidic materials to an access channel formed of segments L1–L4 of microchip device 50. The microchip 50 includes three mixing channels 58A, 58B, and 58C connected along the access channel and in fluid communications with the waste reservoirs 60A, 60B and 60C respectively. Switches 62, 64, or 66 are provided for selectively connecting the waste reservoirs 60A, 60B, and 60C, respectively to ground potential.

The sample and buffer solutions are mixed in mixing channels 58A, 58B, and 58C by way of switches 62, 64, or 66 which are provided for connecting a corresponding one of the waste reservoirs 60A, 60B, or 60C, to ground potential. Thus, when channel 58A is connected to ground, channels 58B and 58C would be disconnected. Thus, for example, in a microchip 50 having access channel lengths L1=L2=L3=L4, the mixing ratio for channel 58A would be 3 parts sample (L1) to 1 part buffer (L2+L3+L4). For channel 58B the mixing ratio would be 1 part sample (L1+L2) to 1 part buffer (L3+L4), and for channel 58C, 1 part sample (L1+L2+L3) to 3 parts buffer (L4). It is to be understood that the channel lengths L1, L2, L3, and L4 of microchip 50 need not be equal so that other mixing ratios can be achieved.

Variable Volume Valve

Figure 5:
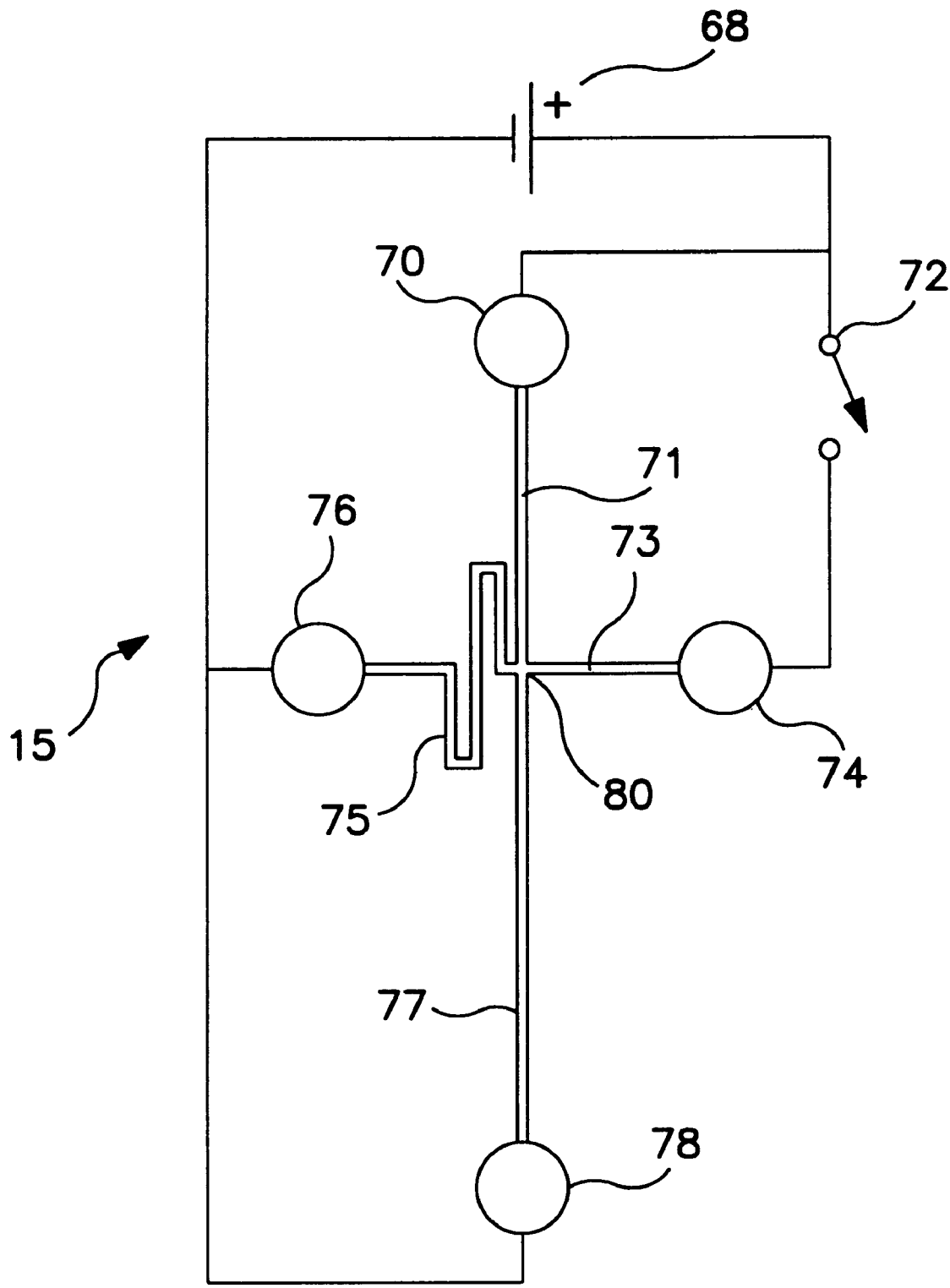
FIG. 5 is a schematic diagram of a microchip in accordance with the present invention that is configured for microfluidic valving.

A schematic of a microchip 15 according to the present invention that demonstrates valving is depicted in FIG. 5. The microchip 15 includes a sample reservoir 70, a buffer reservoir 74, a first waste reservoir 76, and a second waste reservoir 78. A sample channel 71 has a first end in fluidic communication with the sample reservoir 70. A buffer channel 73 has a first end in fluidic communication with the buffer reservoir 74. A first waste channel 75 has one end in fluidic communication with the first waste reservoir 76 and a second waste channel 77 has an end in fluidic communication with the second waste reservoir 78. The four channels intersect at a valving junction 80. The lengths of the various channels between the respective reservoirs and the valving junction are selected to provide predetermined electrical resistance in the respective channels. In this manner, the electric potentials between the various reservoirs and the valve junction 80 can be established using a single high voltage source. In a working example of microchip 15, the channel lengths listed in Table 2 were used.

The sample reservoir 70 is connected to a high voltage supply 68. A switch 72 is connected in series between the high voltage supply 68 and the buffer reservoir 74. The first and second waste reservoirs 76, 78 are connected at a ground potential relative to the high voltage supply 68. The valve 80 is actuated by operating the high voltage switch 72. When switch 72 is closed, the valve 80 is closed and the sample material is electrokinetically transported only to the first waste reservoir 76. When switch 72 is open, the valve 80 is opened and the sample material is transported to both first waste reservoir 76 and second waste reservoir 78. Because the lengths of first waste channel 75 and second waste channel 77 are slightly different, the proportion of sample material transported to the respective waste reservoirs is different. The relative proportions of sample material are determined according to the relative electrical resistances of the first and second waste channels.

Figure 6A:
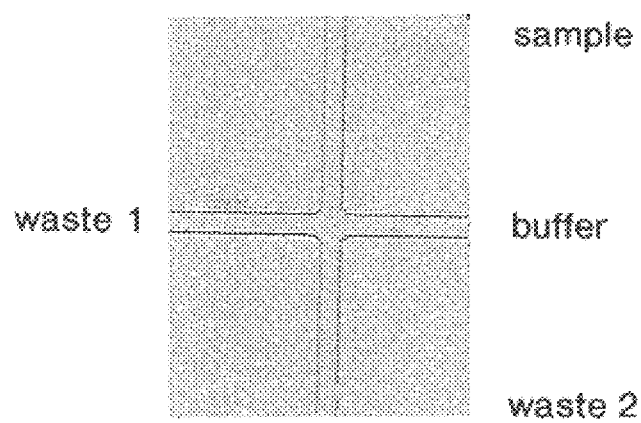
FIG. 6a is a white light image of the dispensing valve of the device shown in FIG. 5.
Figure 6B:
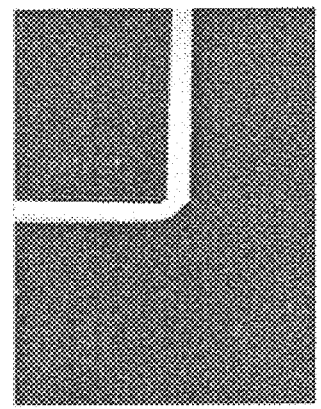
FIG. 6b is a fluorescence image of the valve of FIG. 6a with the valve closed.
Figure 6C:
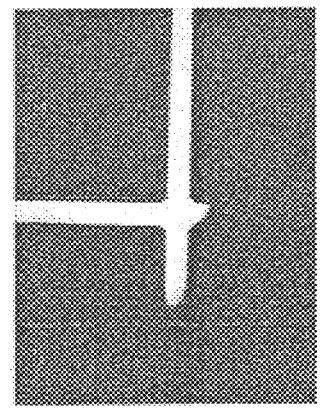
FIG. 6c is a fluorescence image of the valve of FIG. 6a with the valve open.
Figure 6D:
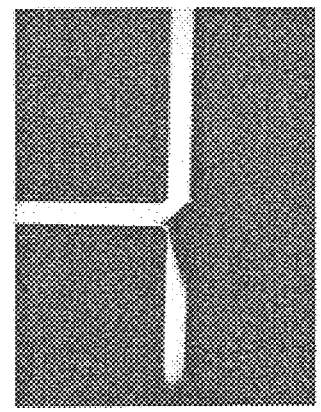
FIG. 6d is a fluorescence image of the valve of FIG. 6a upon reclosing.

To demonstrate the operation of the valve, fluorescent images of an organic dye used in the working example of the microchip 15 are presented in FIGS. 6(a)–6(d). FIG. 6a shows a white light image of the valve junction 80 where the buffer, sample, first waste and second waste channels intersect. FIGS. 6b–6d show transport of the sample material during a sequence of having the valve closed, opened, and reclosed. In FIG. 6b, the switch 72 is closed and a 1 kV potential is applied to the buffer reservoir 74 and sample reservoir 70. Under those conditions the sample material is transported through the valve junction 80 and toward the first waste reservoir 76. In FIG. 6c, the high voltage switch 72 has been opened for 0.4 s and the sample material is transported to both the first waste reservoir 76 and the second waste reservoir 78. The volume of sample material dispensed to the second waste reservoir 78 is proportional to the period of time the high voltage switch 72 is open and to the electric field strength in the analysis channel 77. FIG. 6d shows the sample material plug migrating down the analysis channel after valve 80 has been reclosed by closing the switch 72. The electric field strength in each of the channels when switch 72 is closed are listed in Table 2. The switch 72 can be embodied as any suitable type of switch, including mechanically operated switches, a solenoid-operated switch such as a relay, or a solid state switching device. Alternatively, the function of switch 72 can be performed by cycling the voltage level present between the buffer reservoir 74 and sample reservoir 70 by way of an external control, for example, such as an independently controlled power supply or switching circuit.

TABLE 2

| Channel | Length (mm) | Electric Field Strength (V/cm) with switch closed |
|---|---|---|
| buffer (73) | 7.1 | 400 |
| sample (71) | 14.8 | 190 |
| first waste (75) | 24.2 | 300 |
| second waste (77) | 25.1 | 290 |

Figure 7:
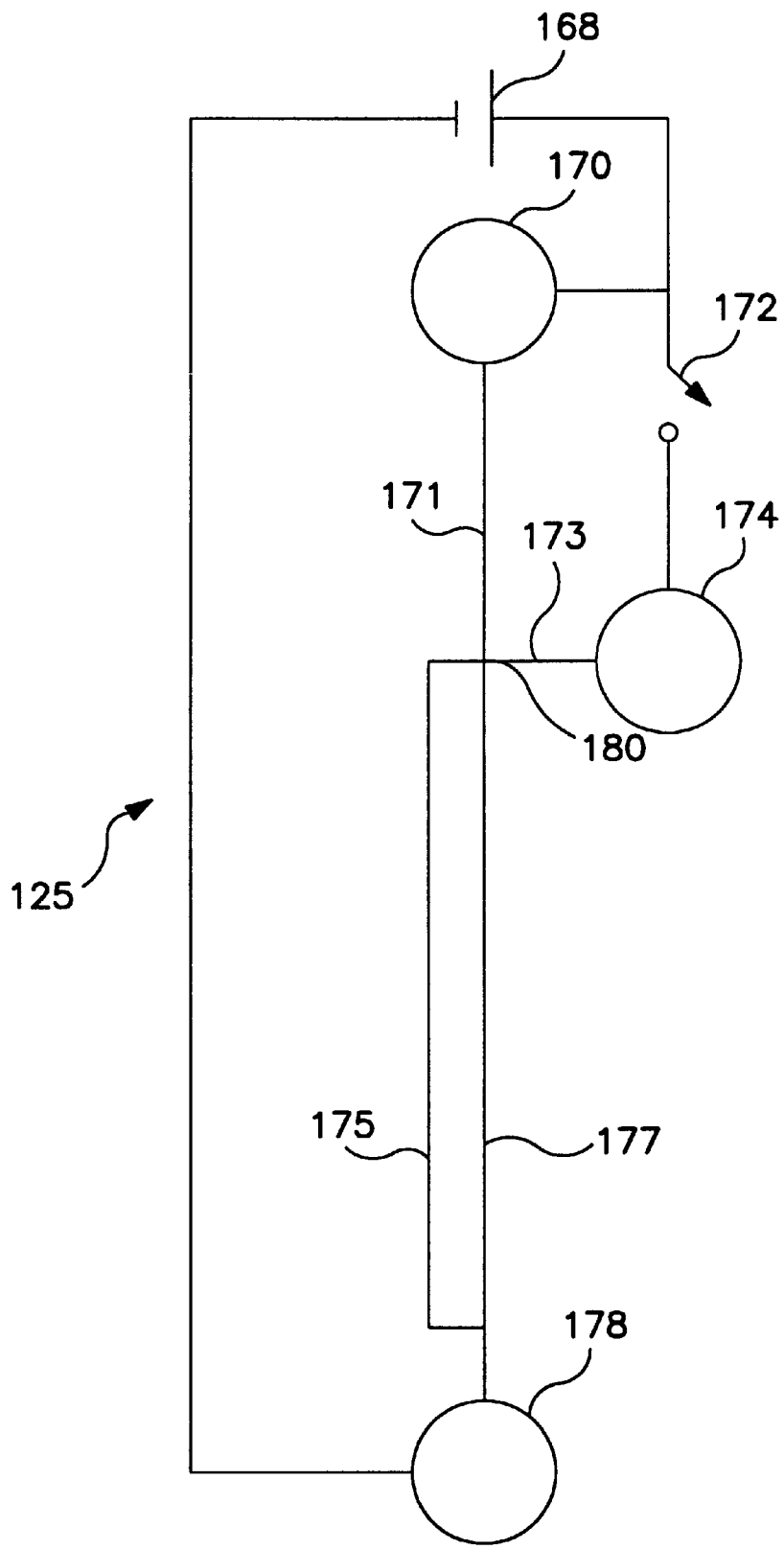
FIG. 7 is a schematic diagram of an alternative embodiment of the microchip shown in FIG. 5.

A further working embodiment demonstrating valving in accordance with the present invention is shown in FIG. 7. The device 125 requires fewer fluidic reservoirs to effect valving than the embodiment shown in FIG. 5. Microchip device 125 reduces the number of waste reservoirs to one because the waste channel 175 and separation channel 177 transport the combined sample and buffer materials to a single waste reservoir 178. The buffer channel 173, sample channel 171, waste channel 175, and the separation channel 177 are dimensioned so as to provide appropriate electrical field strengths in the four channels that intersect at the valve junction 180. For the proper operation of the gated valve, the electrical resistances of the channels are preferably designed so that the electric field strength in the buffer channel 173 is greater than the electric field strength in the separation channel 177 and the electric field strength in the waste channel 175 is greater than the electric field strength in the sample channel 171. Similar to device 15 of FIG. 5, a high voltage power supply 168 is directly connected to the sample reservoir 170 and is connected through the switch 172 to the buffer reservoir 174. The ground side of power supply 168 is operably linked to the waste reservoir 178. The valving device 125 is actuated in essentially the same manner as the device shown in FIG. 5. More specifically, when the electrical switch 172 is opened, the valve 180 is opened, and when the electrical switch 172 is closed, the valve 180 closes.

Reagent Mixing Circuit

Figure 8:
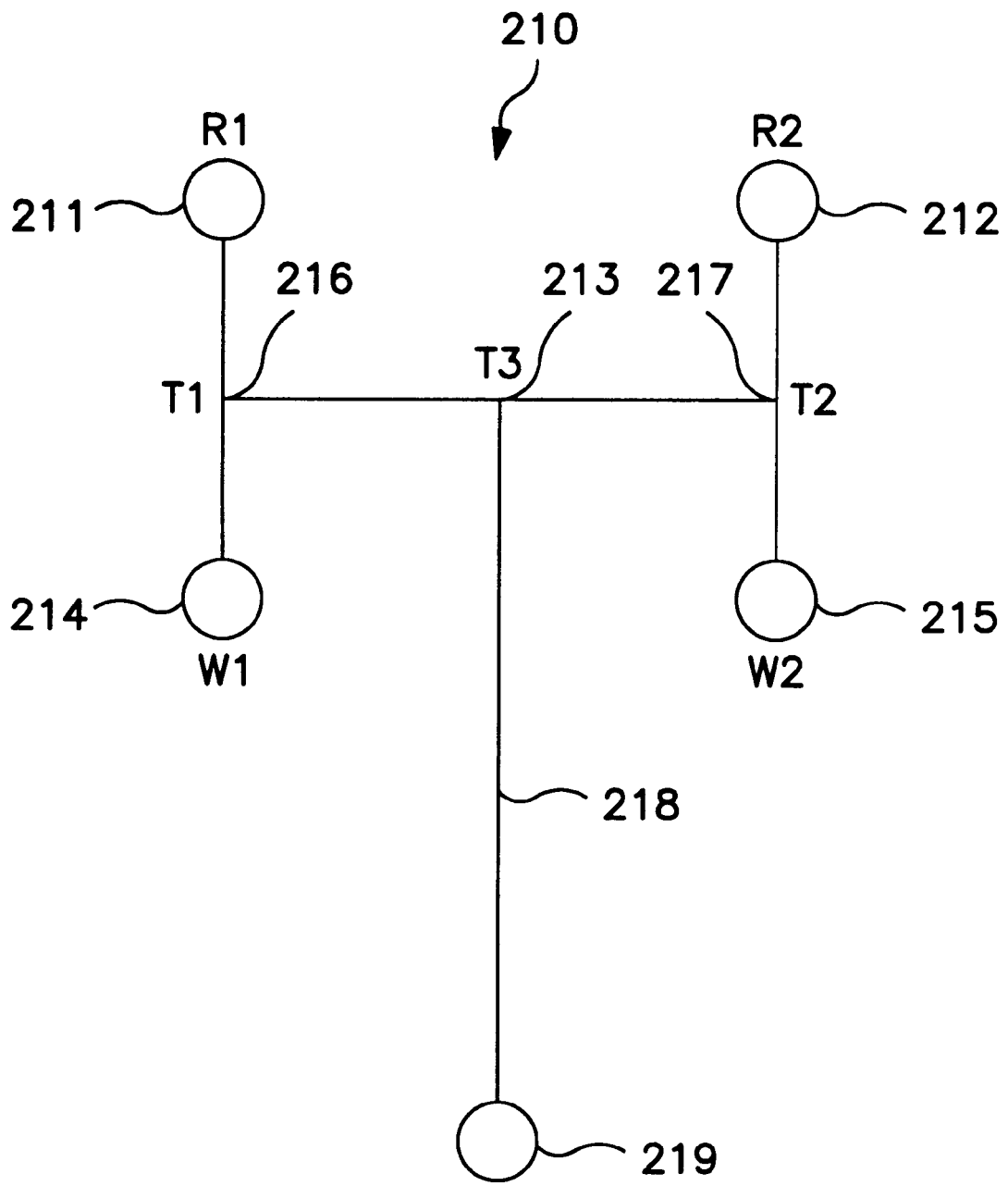
FIG. 8 is a schematic diagram of a reagent mixing circuit in accordance with another aspect of this invention.

Referring now to FIG. 8, there is shown schematically a standard reagent mixing circuit 210 for implementation on a microchip in accordance with the present invention. The mixing circuit 210 electrokinetically mixes a first reagent from R1 reservoir 211 and a second reagent from R2 reservoir 212 at T3 intersection 213 without any potentials applied to the W1 reservoir 214 and the W2 reservoir 215. In this embodiment, the W1 reservoir 214 and the W2 reservoir 215 are used as current shunts to assist in the delivery of low flow rates of the first and second reagents to the T3 intersection 213. The W1 reservoir 214 and the W2 reservoir 215 each contain some appropriate buffer solution for executing electrokinetic manipulations. The use of current shunts permits a wide range of stable mixing ratios for the reagents with minimal requirements for voltage control, signal-to-noise ratio, or digital-to-analog quantization levels. Without current shunts, low or highly precise voltages applied to the reagent reservoirs would be required to pump small volumes of material within the channel manifold. That could lead to unstable delivery of material from the R1 reservoir 211 or the R2 reservoir 212 into the T3 intersection 213, depending on the stability of the power supplies when operating at low potentials or currents.

To deliver a small volume of the first reagent to the T3 intersection 213 using the W1 reservoir 214 as a current shunt, the material is electrokinetically transported from the R1 reservoir 211, and the flow is split at the T1 intersection 216. Controlled portions of the first reagent are sent toward the T3 intersection 213 and the W1 reservoir 214. The ratio of the split portions is determined by the applied potentials and resistances of the channels leading from the R1 reservoir 211 and the W1 reservoir 214. Likewise, to accurately deliver small volumes of the second reagent to the T3 intersection 213 using the W2 reservoir 215 as a current shunt, the material electrokinetically transported from the R2 reservoir 212 is split at the T2 intersection 217, with a portion of the material transported toward the T3 intersection 213 and a second portion transported toward the W2 reservoir 215. This configuration allows delivery of small volumes of material from either the R1 reservoir 211 or the R2 reservoir 212 to the T3 intersection 213, where they are mixed, and avoids having to use low or highly precise voltages applied to the material reservoirs themselves. It is understood that all the electric potentials referred to in connection with the description of this embodiment are relative to the waste reservoir 219.

An alternate operation of the mixing circuit shown in FIG. 8 is to use the W1 reservoir 214 and the W2 reservoir 215 to dilute the reagent materials from the R1 reservoir 211 and the R2 reservoirs 212, respectively, prior to their being mixed at the T3 intersection 213. To dilute the material in the R1 reservoir 211 with material from the W1 reservoir 214, electric potentials are applied to both the R1 reservoir 211 and the W1 reservoir 214 to transport the materials from the respective reservoirs towards the T1 intersection 216. The amount of dilution of the first reagent by the buffer material in the W1 reservoir 214 at the T1 intersection 216 depends on the magnitudes of the potentials applied to the reservoirs and the resistances in the respective channels. Similarly, to dilute the material from the R2 reservoir 212 with the buffer material from the W2 reservoir 215, electric potentials are applied to both the R2 reservoir 212 and the W2 reservoir 215 to transport the materials from the respective reservoirs toward the T2 intersection 217. The amount of dilution of the second reagent by the buffer material in the W2 reservoir 215 at the T2 intersection 217 depends on the magnitudes of the potentials applied to the respective reservoirs and the resistances in the channels. By using the first and second buffers to dilute the first and second reagents, respectively, a wider concentration range of reagents can be reacted at the T3 intersection and studied in the reaction channel 218.

In either of these embodiments, W1 reservoir 214 and the W2 reservoir 215 may be left electrically floating (i.e., with no connection to an external circuit) and the fluidic circuit will function principally like a tee junction similar to that shown in FIG. 1. That is, the first reagent and the second reagent will be mixed in proportions dictated by the applied potentials, the geometry of the channels, and the chemical characteristics of the materials in those channels. It will be appreciated that either of the buffer reservoirs 214 or 215 can be left electrically floating while the other is controlled with a suitable power supply.

Figure 9:
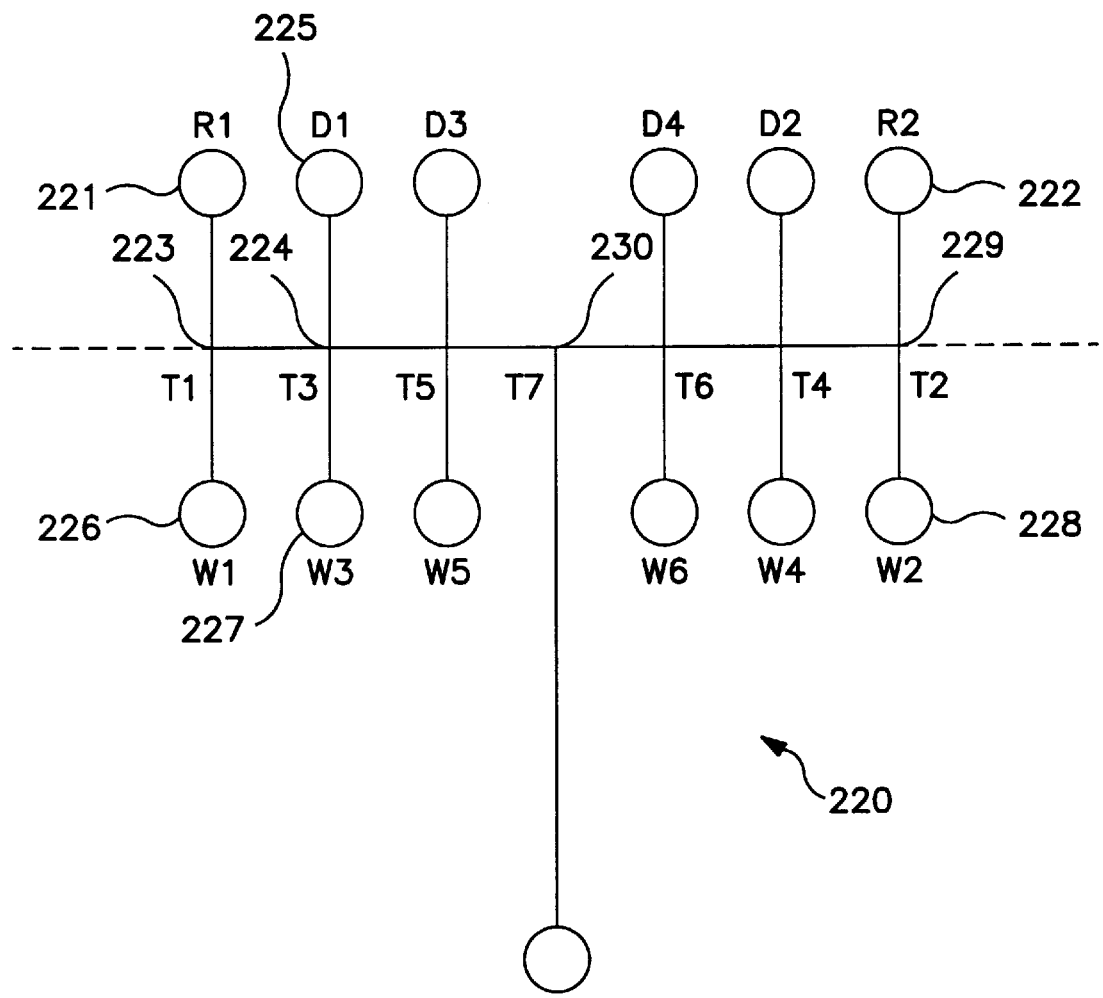
FIG. 9 is a schematic diagram of another embodiment of the reagent mixing circuit shown in FIG. 8.

Referring now to FIG. 9, there is shown an alternate embodiment of the dilution/mixing circuit shown in FIG. 8. In the circuit shown in FIG. 9, multiple fluid shunts are included to provide increased dynamic range over the dilution of either the first reagent in R1 reservoir 221, the second reagent in R2 reservoir 222, or both. The flow of the first reagent through T1 intersection 223 operates just as the corresponding intersection of the embodiment shown in FIG. 8 and described above. The flow of the first reagent from the T1 intersection toward T7 intersection 230 can be further diluted at T3 intersection 224 with a first diluent held in D1 reservoir 225. W3 reservoir 227 allows a material shunting process to occur similar to that which occurs at the T1 intersection 223. This serial dilution process can continue with additional fluidic elements that comprise an input channel, an output channel, a diluent channel, and a shunting channel all connected at a four-way intersection. The reservoirs and intersections on the right hand side of T7 intersection 230 mirror the reservoirs and intersections shown on the left hand side of that intersection. They perform similar operations, but carry out the dilution process on the second reagent which is held in R2 reservoir 222. The circuit depicted schematically in FIG. 9 allows independent control over all of the reagent, diluent, and waste (shunting) reservoirs for maximal control of the process. In general, the diluents would be the same, but they could also be different. An operationally less complex circuit that can perform a similar dilution function can be produced by making the left-hand-side and right-hand-side diluent and waste reservoirs, respectively common. Such a device is shown in FIG. 10 below.

Serial Dilution Circuit

The microfluidic circuit of the present invention can be further embodied as a serial diluter. In a serial diluter according to this invention, a series of channels, tees, and intersections are configured for mixing two reagents (a sample and a buffer) in a series of preselected ratios. The desired dilutions correspond to the current flow in the various channels of the microchip. Therefore, a microchip for implementing this aspect of the present invention is designed by analyzing the various channels as an equivalent electrical circuit. Each channel or circuit branch has a resistance designed to provide a desired electrical current therethrough. The sample and buffer materials are transported through the various microchannels in direct proportion to the equivalent current flow. FIG. 10 shows a preferred microfluidic circuit 810 for a serial diluter in accordance with this aspect of the present invention.

Figure 10:
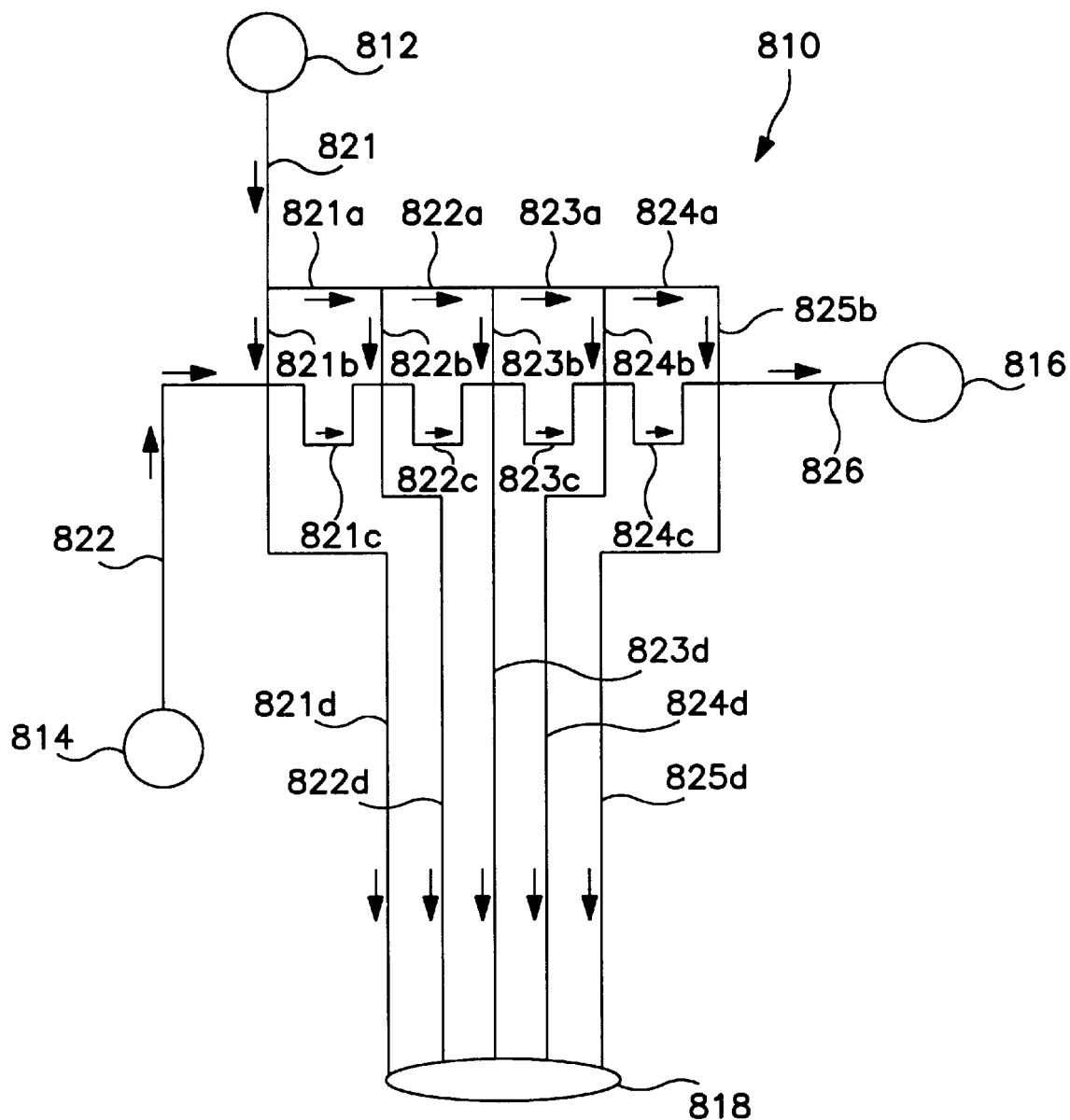
FIG. 10 is a schematic diagram of a fluidic microchip for performing multiple serial dilutions in accordance with another embodiment of this invention.

Referring now to FIG. 10, the serial diluter circuit 810 includes a buffer reservoir 812 for holding a buffering material or other diluent, a sample reservoir 814 for holding a sample material, a first waste reservoir 816, and a second waste reservoir 818. A main buffer channel 821 in fluid communication with the buffer reservoir 812 is formed for carrying the buffer material. A sample channel 822 is in fluid communication with the sample reservoir 814 for carrying the sample material.

A plurality of buffer channel extensions 821a, 822a, 823a, and 824a extend in series from the buffer channel 821. A set of buffer branch channels 821b, 822b, 823b, 824b, and 825b each branch off from the buffer channel extensions 821a, 822a, 823a, and 824a, respectively, at selected locations relative to the intersection with the main buffer channel 821. The sample channel 822 interconnects with the buffer branch channel 821b at a preselected distance from the intersection with the first buffer extension channel 821a. A mixing channel 821c interconnects with the buffer branch channel 821b at the point of intersection with sample channel 822. A series of mixing channels 822c, 823c, and 824c extend from the other end of mixing channel 821c. A set of analysis channels 821d, 822d, 823d, 824d, and 825d branch off from the mixing channels 821c, 822c, 823c, and 824c, respectively, at selected locations relative to the intersection with the branch channel 821b. In the embodiment shown in FIG. 10, the analysis channels branch off at respective ends of the mixing channels. The analysis channels have different lengths relative to one another and are in fluid communication with the second waste reservoir 818. A waste channel 826 interconnects the end of mixing channel 824c with the first waste channel 816.

When a single voltage is applied to the buffer reservoir 812 and the sample reservoir 814 relative to the waste reservoirs 816 and 818, the buffer material is electrokinetically transported along buffer channel 821 into buffer channel extension 821a and buffer branch channel 821b. The buffer material is similarly transported from buffer branch channel 821b into mixing channel 821c. Arrows indicate the buffer flow direction in the drawing. Simultaneously, the sample material is electrokinetically transported along sample channel 822 into mixing channel 821c and analysis channel 821d as indicated by the arrows in FIG. 10. The sample material is diluted with the buffer material in mixing channel 821c, whereas the sample material in analysis channel 821d is at the same concentration as the sample material in sample channel 822, i.e., it is undiluted.

As the process continues, the buffer material in buffer extension channel 821a is split between buffer extension channel 822a and buffer branch channel 822b. The buffer material in branch channel 822b flows into mixing channel 822c and the diluted sample material in mixing channel 821c is split between mixing channel 822c and analysis channel 822d. The diluted sample material from mixing channel 821c is further diluted in mixing channel 822c, whereas the diluted sample material in analysis channel 822d is at the same concentration as the diluted sample material in mixing channel 821c.

It can be readily appreciated that further splitting and dilution of the sample and buffer materials is accomplished in a similar fashion with buffer extension channels 823a and 824a, buffer branch channels 823b, 824b, and 825b, mixing channels 823c and 824c, and analysis channels 823d, 824d, and 825d. In the embodiment shown in FIG. 10, there are five analysis channels, but the series of channel extensions, channel branches, mixing channels, and analysis channels can continue for as many dilutions as needed for a particular process.

In the embodiment of FIG. 10, the channels are formed with essentially the same cross-sectional areas. The channel resistance is increased by lengthening the channel or decreased by shortening the channel during design and fabrication of the microchip. Use of relatively narrow cross sections for the mixing channels is preferred because it allows rapid equilibration of the mixed fluid streams.

Figure 11A:
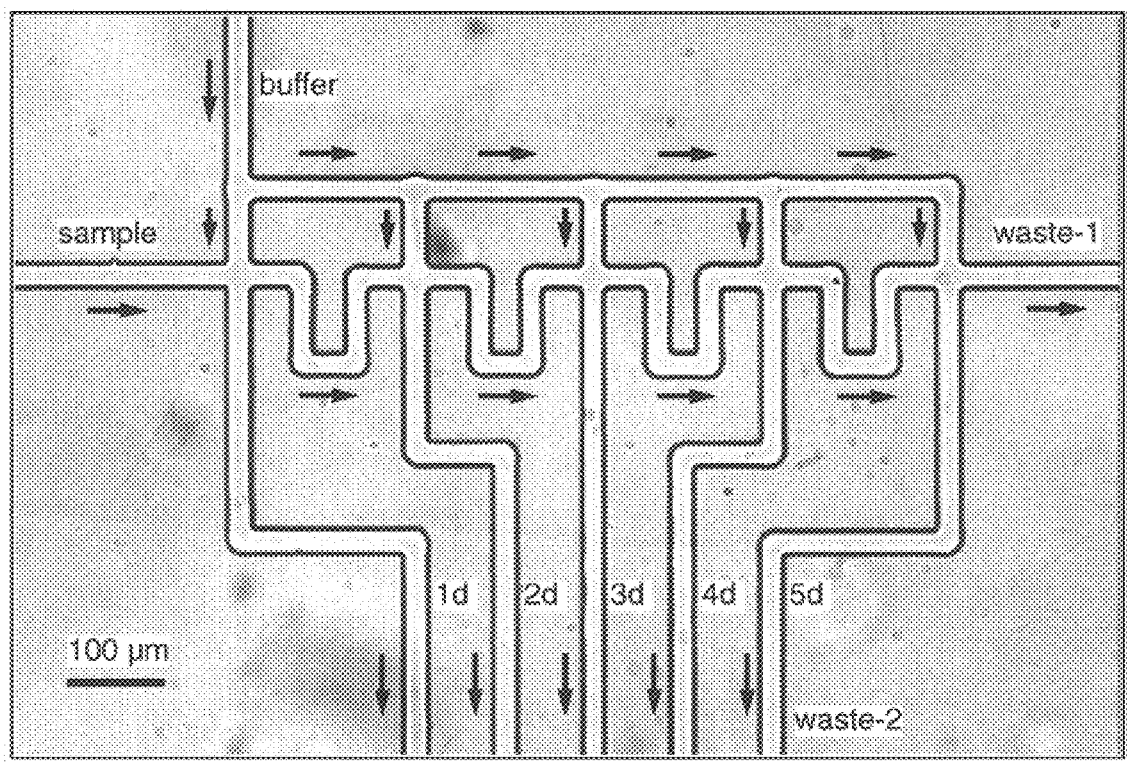
FIG. 11(a) is a CCD image of an actual dilution manifold that corresponds to the diagram of FIG. 10.

As an example of the serial diluter described above and shown in FIG. 10, a microchip device having the channel structure shown in FIG. 10 was fabricated. A CCD image of the actual embodiment of the serial diluter circuit 810 is shown in FIG. 11(a). The various sample and buffer channels were dimensioned to proportionally dilute the sample material at various concentrations. The channel dimensions were selected to provide the following sample dilutions: channel 821d, 100% sample; channel 822d, 38% sample and 62% buffer; channel 823d, 22% sample and 78% buffer; channel 824d, 14% sample and 86% buffer; and channel 825d, 6% sample and 94% buffer. The lengths of the various channels on the microchip are presented in Table 3 below in millimeters (mm).

TABLE 3

| Channel ID | Length |
| --- | --- |
| Buffer Channel 821 | 5.7 mm |
| Sample Channel 822 | 15.6 mm |
| Buffer Extension Channels 821a, 822a, 823a, and 824a | 0.2 mm each |
| Buffer Branch Channels 821b, 822b, 823b, 824b, and 825b | 0.1 mm each |
| Mixing Channels 821c, 822c, 823c, and 824c | 0.4 mm each |
| Waste Channel 826 | 5.0 mm |
| Analysis Channel 821d | 12.0 mm |
| Analysis Channel 822d | 11.9 mm |
| Analysis Channel 823d | 11.8 mm |
| Analysis Channel 824d | 11.9 mm |
| Analysis Channel 825d | 12.0 mm |

Figure 11B:
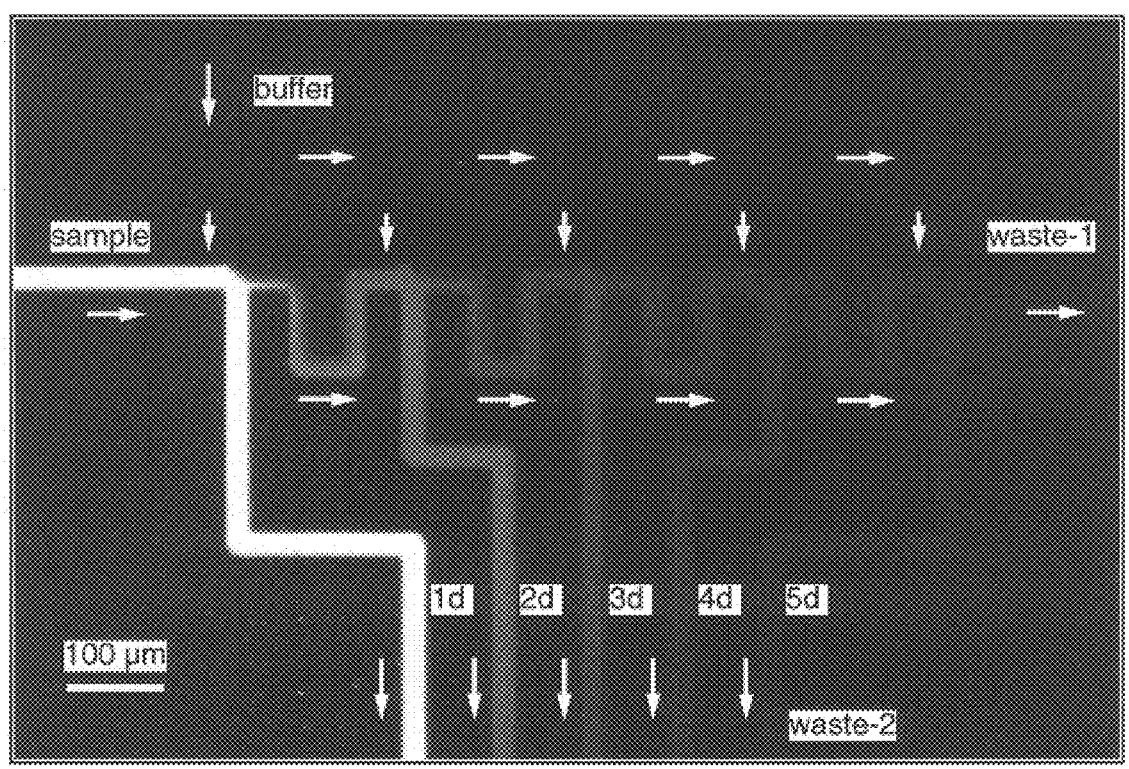
FIG. 11(b) is a fluorescence image of the dilution manifold of FIG. 11(a) showing the performance of a multiple dilution experiment.
Figure 12:
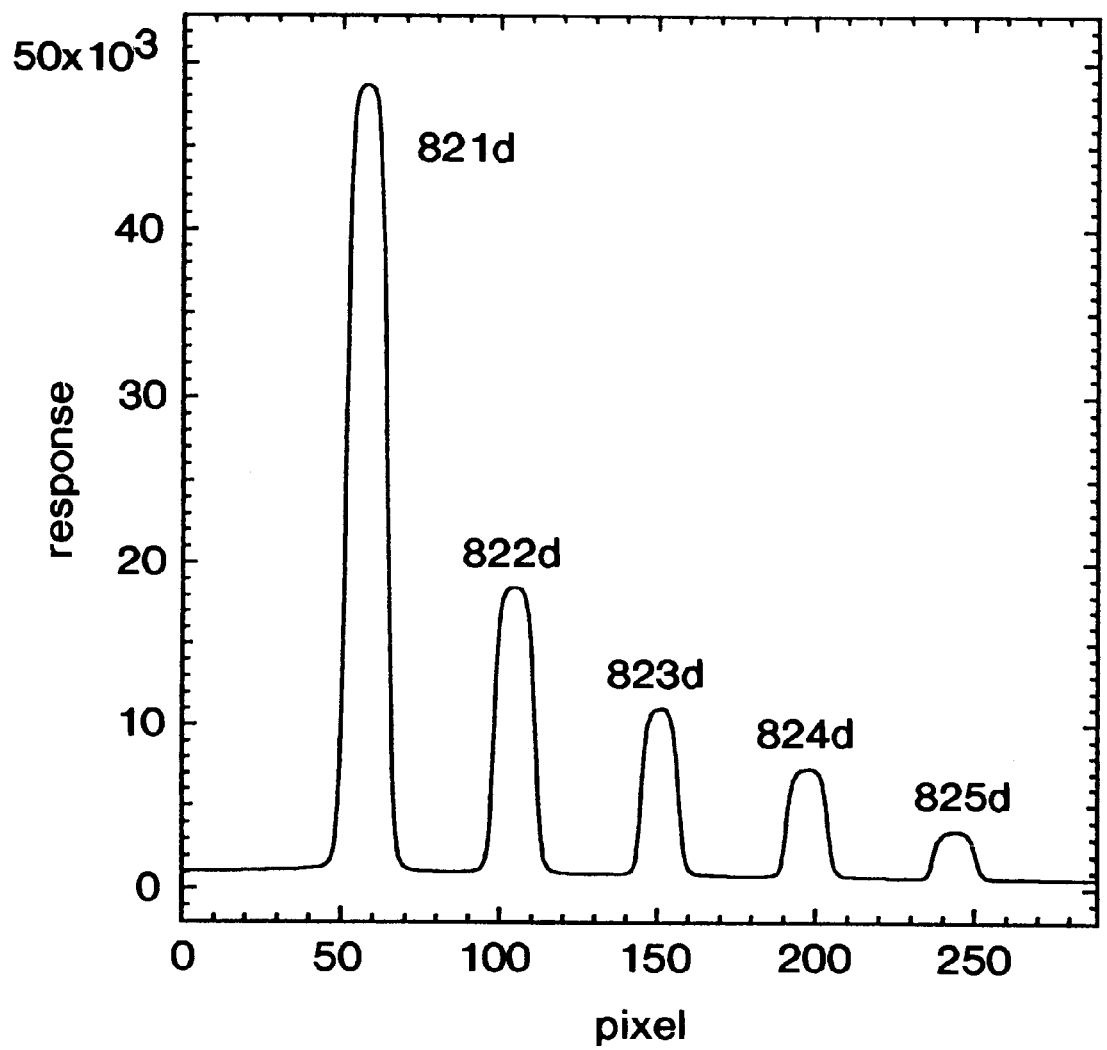
FIG. 12 is a graph of the average fluorescence signal obtained for each of the analysis channels during the multiple dilution experiment shown in FIG. 11(b).

An experiment was run using the microchip for serially diluting a sample material (100 μM rhodamine B in 20 mM sodium tetraborate) with a buffer material (20 mM sodium tetraborate). The sample and buffer reservoirs were filled with the respective sample and buffer materials. A 400 volt potential was applied to the sample and buffer reservoirs while the waste reservoirs were maintained at ground potential. FIG. 11(b) is a fluorescence image showing the progressive dilution of the sample, which is readily observable in the successive analysis channels. The average fluorescence intensity of the respective analysis channels is plotted in FIG. 12 as a function of pixel position. The calculated and measured dilution ratios for the diluted material in each analysis channel are set forth in Table 4.

TABLE 4

| Channel | Relative Dilution (Calculated) | Relative Dilution (Measured) |
| --- | --- | --- |
| 821d | 1.0 | 1.0 |
| 822d | 0.37 | 0.36 |
| 823d | 0.22 | 0.21 |
| 824d | 0.12 | 0.13 |
| 825d | 0.052 | 0.059 |

The data presented in Table 4 show that there is good correlation between the theoretical and actual dilution ratios. The calculated relative dilutions are corrected for slight variations in channel widths. Also, the measured relative dilutions are corrected for nonuniform excitation for the fluorescence measurements.

In view of the foregoing disclosure, it can be seen that the microfabricated device in accordance with the present invention readily provides microfluidic proportioning. Such functionality is useful in analyzing chemical and biological reactions such as kinetics studies requiring the combination of materials in precise volumes. The microfabricated device disclosed herein enables the on-chip mixing of materials in different proportions using channels having different electrical resistances. The microfabricated device includes one or more channel junctions or "tees" having sample and buffer reagent channels that meet at a mixing junction. By having tributary channels with the same cross sectional area but different lengths, the materials traveling therethrough, can be mixed at a junction depending on the ratio of the channel lengths, because the electrical resistances of the microfabricated channels are directly proportional to the channel length. Microfabricated channels having different cross-sectional areas could also effectively proportion samples, because the microchannel resistance is inversely proportional to cross-sectional area. As such, handling of the voltage division on the microchip can be accomplished by properly dimensioning the channels of the microfabricated device without using techniques external to the microchip. In this way, the number of voltage sources needed to operate a microfluidic device can be greatly reduced. Furthermore, by appropriate arrangement and dimensioning of the microchannels and their interconnections, the number of sample, buffer, and waste reservoirs needed to perform multiple dilutions of a sample material can be significantly reduced.

The terms and expressions which have been employed are used as terms of description and not of limitation. There is no intention in the use of such terms and expressions of excluding any equivalents of the features shown and described or portions thereof. For example channel resistance can be varied by altering channel width or height as well as length to facilitate compact microfluidic designs. It is recognized, however, that various modifications such as channel dimension, location, and arrangement are possible within the scope of the invention as claimed.

That which is claimed is:

1. An apparatus for effecting microfluidic manipulation comprising:
    a first reservoir adapted for containing a first material;
    a second reservoir adapted for containing a second material;
    a third reservoir adapted for containing a third material;
    a first channel having a first end in fluidic communication with said first reservoir;
    a second channel having a first end in fluidic communication with said second reservoir;
    a third channel having a first end in fluidic communication with said third reservoir;
    said first, second, and third channels having respective second ends that are interconnected to form a junction; and
    a source of electrical potential operatively connected to said first, second, and third fluid reservoirs for effecting electrokinetic transport of the first and second materials from said first and second reservoirs toward said third reservoir;
    wherein the lengths, cross-sections, or combinations thereof, of the first, second, and third channels are dimensioned to provide mixing of the first and second materials at said junction in a first ratio upon application of the electric potential to said reservoirs.

2. The apparatus of claim 1 wherein said first, second, and third channels have the same cross-sectional dimension and the lengths of said channels are formed to provide mixing of the first material and the second material at said junction in the first ratio.

3. The apparatus of claim 1 wherein said source of electric potential is adapted to provide a single voltage to said first and second reservoirs relative to said third reservoir.

4. The apparatus of claim 3 wherein said source of electric potential comprises a power supply having a first potential and a second potential, said first potential being operatively connected to said first and second reservoirs and said second potential being operatively connected to said third reservoir.

5. Apparatus as set forth in claim 1 comprising:
    a fourth reservoir adapted for containing a fourth material;
    a fourth channel having a first end in fluidic communication with said fourth reservoir;
    a fifth channel having a first end in fluidic communication with said first reservoir; and
    a sixth channel having a first end in fluidic communication with said second reservoir;
    said fourth, fifth, and sixth channels having respective second ends that are interconnected to form a second junction;
    wherein the lengths, cross-sections, or combinations thereof, of the fourth, fifth, and sixth channels are dimensioned to provide mixing of the first and second fluidic materials at said second junction in a second ratio upon application of the electric potential to said reservoirs.

6. Apparatus as set forth in claim 1 comprising:
    a fourth channel having a first end in fluidic communication with said first reservoir;
    a fifth channel having a first end in fluidic communication with said second reservoir; and
    a sixth channel having a first end in fluidic communication with said third reservoir;
    said fourth, fifth, and sixth channels having respective second ends that are interconnected to form a second junction;
    wherein the lengths, cross-sections, or combinations thereof, of the fourth, fifth, and sixth channels are dimensioned to provide mixing of the first and second fluidic materials at said second junction in a second ratio upon application of the electric potential to said reservoirs.

7. Apparatus as set forth in claim 1 comprising:
    a plurality of first channels each having a first end in fluidic communication with said first reservoir;
    a plurality of second channels having a first end in fluidic communication with said second reservoir;
    a plurality of third channels each having a first end in fluidic communication with said third reservoir;
    said pluralities of first, second, and third channels each having respective second ends that are respectively interconnected to form a plurality of junctions; and
    a source of electrical potential operatively connected to said first, second, and third fluid reservoirs for effecting electrokinetic transport of the first and second fluidic materials from said first and second reservoirs toward said third reservoir;
    wherein the lengths, cross-sections, or combinations thereof, of the each of the first, second, and third channels are dimensioned to provide mixing of the first and second fluidic materials in a plurality of ratios upon application of the electric potential to said reservoirs such that a desired mixing ratio is provided at each of said plurality of junctions.

8. The apparatus of claim 7 wherein said pluralities of first, second, and third channels have the same cross-sectional dimension and the lengths of said channels are formed to provide the mixing of the first fluidic material and the second fluidic material at said plurality of junctions in the plurality of ratios.

9. The apparatus of claim 7 wherein said second reservoir comprises a plurality of second reservoirs.

10. The apparatus of claim 9 wherein pairs of said plurality of second channels have their first ends in fluidic communication with respective ones of said plurality of second reservoirs.

11. The apparatus of claim 1 wherein said first reservoir comprises a plurality of first reservoirs, said second reservoir comprises a plurality of second reservoirs, said first channel comprises a plurality of first channels each having a first end in fluidic communication with respective ones of said plurality of first reservoirs, said second channel comprises a plurality of second channels each having a first end in fluidic communication with respective ones of said plurality of second reservoirs, and said third channel comprises a plurality of third channels each having a first end in fluidic communication with said third reservoir; said pluralities of first, second, and third channels each having respective second ends that are respectively interconnected to form a plurality of junctions; and the lengths, cross-sections, or combinations thereof, of the each of the pluralities of first, second, and third channels are dimensioned to provide mixing of the first and second fluidic materials in a plurality of ratios upon application of the electric potential to said reservoirs such that a desired mixing ratio is provided at each of said plurality of junctions.

12. An apparatus for effecting microfluidic manipulation comprising:

a first reservoir adapted for containing a first material;

a second reservoir adapted for containing a second material;

a first receiving reservoir adapted for containing a third material;

a second receiving reservoir adapted for containing a fourth material;

a first channel having a first end in fluidic communication with said first reservoir and a second end in fluidic communication with said second reservoir;

a second channel having a first end in fluidic communication with said first receiving reservoir and a second end interconnected with said first channel to form a first junction;

a third channel having a first end in fluidic communication with said second receiving reservoir and a second end interconnected with said first channel to form a second junction;

a switch operatively connected to said first and second receiving reservoirs; and a source of electrical potential operatively connected to said first and second reservoirs and said switch, whereby said electrical potential can be selectively connected to either said first receiving reservoir or said second receiving reservoir for effecting electrokinetic transport of the first and second materials from said first and second reservoirs toward said first or said second receiving reservoir;

wherein the first junction is positioned along said first channel to provide mixing of the first and second materials at said first junction in a first ratio upon application of the electric potential to said first and second reservoirs relative to said first receiving reservoir and the second junction is positioned along said first channel to provide mixing of the first and second materials at said second junction in a second ratio upon application of the electric potential to said first and second reservoirs relative to said second receiving reservoir.

13. The apparatus set forth in claim 12 wherein said switch comprises:

a first switch operatively connected between said source of electric potential and said first receiving reservoir; and a second switch operatively connected between said source of electric potential and said second receiving reservoir;

whereby the first and second materials are selectively transported to the first or second receiving reservoirs by closing the first switch or the second switch, respectively.

14. The apparatus as set forth in claim 12 wherein said receiving reservoir comprises a plurality of receiving reservoirs and said apparatus comprises a plurality of channels each having a first end in fluidic communication with a corresponding one of said plurality of receiving reservoirs and second ends interconnected with said first channel to form a plurality of junctions, wherein the plurality of junctions are positioned along said first channel to provide mixing of the first and second materials in a different ratio at each of said plurality of junctions upon application of the electric potential to said reservoirs.

15. The apparatus as set forth in claim 14 comprising a plurality of switches each of which is operatively connected between one of said plurality of receiving reservoirs and the source of electric potential whereby the first and second materials are selectively transported in a desired mixing ratio to one of the plurality of receiving reservoirs by closing one of said plurality of switches.

16. An apparatus for effecting microfluidic manipulations comprising:

a first reservoir adapted for containing a first material;

a second reservoir adapted for containing a second material;

a third reservoir adapted for containing a third material;

a fourth reservoir adapted for containing a fourth material;

a first channel having a first end in fluidic communication with said first reservoir;

a second channel having a first end in fluidic communication with said second reservoir;

a third channel having a first end in fluidic communication with said third reservoir;

a fourth channel having a first end in fluidic communication with said fourth reservoir;

said first, second, third, and fourth channels having respective second ends that are interconnected to form a junction;

a first source of electrical potential operatively connected to said first and second reservoirs and a second source of electrical potential applied to said third and fourth reservoirs for effecting electrokinetic transport of the first and second materials from said first and second reservoirs toward said third and fourth reservoirs; and a switch operatively connected between said first reservoir and said first source of electric potential;

wherein the lengths, cross-sections, or combinations thereof, of the first, second, third, and fourth channels are dimensioned such that (i) when said switch is closed, the first material is transported toward said third and fourth reservoirs and said second material is transported toward said third reservoir and (ii) when said switch is opened, said second material is transported toward said fourth reservoir.

17. An apparatus for effecting microfluidic manipulations comprising:

a first reservoir adapted for containing a first material;

a second reservoir adapted for containing a second material;

a third reservoir adapted for containing a third material;

a first channel having a first end in fluidic communication with said first reservoir;

a second channel having a first end in fluidic communication with said second reservoir;

a third channel having a first end in fluidic communication with said third reservoir;

a fourth channel having a first end in fluidic communication with said third reservoir;

said first, second, third, and fourth channels having respective second ends that are interconnected to form a junction;

a first source of electrical potential operatively connected to said first and second reservoirs and a second source of electrical potential operatively connected to said third fluid reservoir for effecting electrokinetic transport of the first and second materials from said first and second reservoirs toward said third reservoir; and a switch operatively connected between said first reservoir and said first source of electric potential;

wherein the lengths, cross-sections, or combinations thereof, of the first, second, third, and fourth channels are dimensioned such that (i) when said switch is closed, the first material is transported through said third and fourth channels to said third reservoir and the second material is transported through the third channel to the third reservoir and (ii) when said switch is opened, the second material is transported through said fourth channel to said third reservoir.

18. An apparatus for effecting microfluidic manipulation comprising:

a first reservoir adapted for containing a first material;

a second reservoir adapted for containing a second material;

a third reservoir adapted for containing a third material;

a fourth reservoir adapted for containing a fourth material;

a first channel having a first end in fluidic communication with said first reservoir;

a second channel having a first end in fluidic communication with said second reservoir;

a third channel having a first end in fluidic communication with said third reservoir;

a fourth channel having a first end in fluidic communication with said fourth reservoir;

said first, second, third, and fourth channels having respective second ends that are interconnected to form a first junction; and sources of electrical potential operatively connected to said first, second, third, and fourth fluid reservoirs for effecting electrokinetic transport of the first and second material toward said third and fourth reservoirs;

wherein when the electrical potentials are applied the first material is transported toward said third and fourth reservoirs and the second material is transported toward said third reservoir such that the first and second materials are mixed in a controlled proportion in the third channel.

19. The apparatus of claim 18 wherein a first source of electrical potential is connected to said first and second reservoirs and a second source of electrical potential is applied to said third and fourth reservoirs; and the lengths, cross-sections, or combination thereof, of the first, second, third, and fourth channels are dimensioned such that the first material is transported toward said third and fourth reservoirs and the second material is transported toward said third reservoir such that the first and second materials are mixed in a controlled proportion in the third channel.

20. The apparatus of claim 19 wherein the second electrical potential is ground.

21. The apparatus set forth in claim 18 comprising:

a fifth reservoir adapted for containing a fifth material;

a sixth reservoir adapted for containing a sixth material;

a fifth channel having a first end in fluidic communication with the fifth reservoir, a second end in fluidic communication with the sixth reservoir;

said fifth channel intersecting with said third channel to form a second junction between the first junction and the third reservoir; and sources of electrical potential operatively connected to said first, second, third, fourth, fifth, and sixth fluid reservoirs for effecting electrokinetic transport of the first, second, and fifth material toward said third, fourth, and sixth reservoirs;

wherein when the electrical potentials are applied the first material is transported toward said third and fourth reservoir; the second material is transported toward said third reservoir such that the first and second materials are mixed in controlled proportions in the third channel; said mixed first and second materials are transported toward the sixth reservoir and the fifth material and the mixed first and second materials are transported toward the third reservoir such that they are mixed in a controlled fashion.

22. The apparatus set forth in claim 18 comprising:

a fifth channel having a first end in fluidic communication with the second reservoir, a second end in fluidic communication with the fourth reservoir;

said fifth channel intersecting with said third channel to form a second junction between the first junction and the third reservoir;

wherein the lengths, cross-sections, or combination thereof, of the first, second, third, fourth, and fifth channels are dimensioned such that when the electrical potentials are applied the first material is transported toward said third and fourth reservoir; the second material is transported toward said third reservoir such that the first and second materials are mixed in controlled proportions in the third channel; said mixed first and second materials are transported toward the fourth reservoir through the second junction and the second material and the mixed first and second materials are mixed at the second junction and transported toward the third reservoir such that they are mixed in a controlled fashion.

* * * * *